United States Patent
Lin et al.

(10) Patent No.: US 9,738,871 B2
(45) Date of Patent: Aug. 22, 2017

(54) METHOD OF EXTRACTING ORGANELLES FROM CELLS

(71) Applicant: TAIWAN MITOCHONDRION APPLIED TECHNOLOGY CO., LTD., Zhubei, Hsinchu County (TW)

(72) Inventors: Chia-Wen Lin, Zhubei (TW); Hsin-Ting Tsai, Zhubei (TW); Han-Chung Cheng, Zhubei (TW)

(73) Assignee: TAIWAN MITOCHONDRION APPLIED TECHNOLOGY CO., LTD., Zhubei (TW)

( * ) Notice: Subject to any disclaimer, the term of this patent is extended or adjusted under 35 U.S.C. 154(b) by 218 days.

(21) Appl. No.: 14/844,692

(22) Filed: Sep. 3, 2015

(65) Prior Publication Data
US 2016/0257924 A1 Sep. 8, 2016

(30) Foreign Application Priority Data

Mar. 4, 2015 (TW) .............................. 104106905 A

(51) Int. Cl.
*C12N 5/00* (2006.01)
(52) U.S. Cl.
CPC ...................... *C12N 5/00* (2013.01)
(58) Field of Classification Search
CPC ...................................................... C12N 5/00
USPC ............................................................ 241/2
See application file for complete search history.

(56) References Cited

U.S. PATENT DOCUMENTS

| | | | | |
|---|---|---|---|---|
| 3,773,468 A | * | 11/1973 | Hubbard | B01L 3/5021 215/379 |
| 4,828,395 A | * | 5/1989 | Saito | C12M 47/06 241/2 |
| 5,464,773 A | * | 11/1995 | Melendez | C12M 47/06 241/175 |
| 5,829,696 A | * | 11/1998 | DeStefano | G01N 1/286 241/169 |
| 6,235,501 B1 | * | 5/2001 | Gautsch | C12N 15/1003 241/2 |
| 8,286,899 B2 | * | 10/2012 | Schowalter | C12M 45/02 241/2 |

* cited by examiner

*Primary Examiner* — Mark Rosenbaum
(74) *Attorney, Agent, or Firm* — Maschoff Brennan

(57) ABSTRACT

A method of extracting organelles from cells includes following process. A plurality of cells and a solution are mixed uniformly to obtain a mixture. The mixture is loaded into a container. The container is placed in a milling device comprising a miller and a mechanical power source connected to the miller. The miller is immersed into the mixture within the container. The mixture is milled by the miller to obtain a homogenized mixture, wherein a milling parameter is provided to the milling device, and the mechanical power source drives the miller according to the milling parameter. The homogenized mixture is centrifuged to obtain a supernatant. The supernatant is centrifuged to obtain a precipitate with a plurality of organelles. In the process that the mixture is milled by the miller, at least a part of the miller is kept in the mixture.

10 Claims, 2 Drawing Sheets

METHOD OF EXTRACTING ORGANELLES FROM CELLS

CROSS-REFERENCE TO RELATED APPLICATIONS

This non-provisional application claims priority under 35 U.S.C. §119(a) on Patent Application No(s). 104106905 filed in Taiwan, R.O.C. on 4 Mar., 2015, the entire contents of which are hereby incorporated by reference.

TECHNICAL FIELD

The disclosure relates to a method of extracting organelle from cells, more particularly to a method of extracting organelle from cells by milling the cells using a miller.

BACKGROUND

Organelles are specialized subunits within a cell and have specific functions. Mitochondrion is a kind of the organelles where oxidative phosphorylation and adenosine triphosphate (ATP) synthesis take place. The adenosine triphosphate (ATP) is used as an energy source of metabolic processes in cells so that the mitochondrion is also described as cellular power plants. Except for providing energy to cell, the mitochondrion is involved in other processes, including signaling, cellular differentiation, cell death, as well as the control of the cell cycle and cell growth. Analysis of mitochondrial DNA can help researches about genetics and hereditary diseases. Therefore, developing a method to extract the mitochondria from cell without damaging the mitochondria can facilitate the researches about genetics and hereditary diseases.

Conventional manners of extract organelles from cells are rupturing cell membranes through chemical or physical ways to extract organelles within the cells. However, the conventional manners have a problem that membranes of the organelles are also damaged when the cell membranes are ruptured through the chemical or physical ways so that only a few of the organelles can be extracted from the cells, intactly. Thus, developers try to rupture the cell membranes to extract organelles from the cells without damaging the organelles.

SUMMARY

According to one embodiment of the present disclosure, a method of extracting organelles from cells includes following steps. A plurality of cells and a solution are mixed uniformly to obtain a mixture. The mixture is loaded into a container. The container with the mixture inside is placed in a milling device, wherein the milling device comprises a miller and a mechanical power source connected to the miller. The miller is immersed into the mixture within the container. The mixture is milled by the miller of the milling device to obtain a homogenized mixture, wherein a milling parameter is provided to the milling device, and the mechanical power source drives the miller according to the milling parameter. The homogenized mixture is centrifuged to obtain a supernatant. The supernatant is centrifuged to obtain a precipitate with a plurality of organelles. In the process that the mixture is milled by the miller of the milling device to obtain a homogenized mixture, at least a part of the miller is kept in the mixture.

According to another embodiment of the present disclosure, a method of extracting organelles from cells includes following steps. A plurality of cells and a solution are uniformly mixed to obtain a mixture. The mixture is loaded into a container. The mixture in the container is milled to obtain a homogenized mixture by rotating a miller relative to the container along a central axis of the container as a rotating axis and reciprocating the miller relative to the container along the central axis of the container. The homogenized mixture is centrifuged to obtain a supernatant. The supernatant is centrifuged to obtain a precipitate with a plurality of organelles. In the process that the mixture is milled by the miller of the milling device to obtain a homogenized mixture, at least a part of the miller is kept in the mixture.

BRIEF DESCRIPTION OF THE DRAWINGS

The present disclosure will become more fully understood from the detailed description given hereinbelow and the accompanying drawings which are given by way of illustration only and thus are not limitative of the present application and wherein.

DETAILED DESCRIPTION

Figure 1:
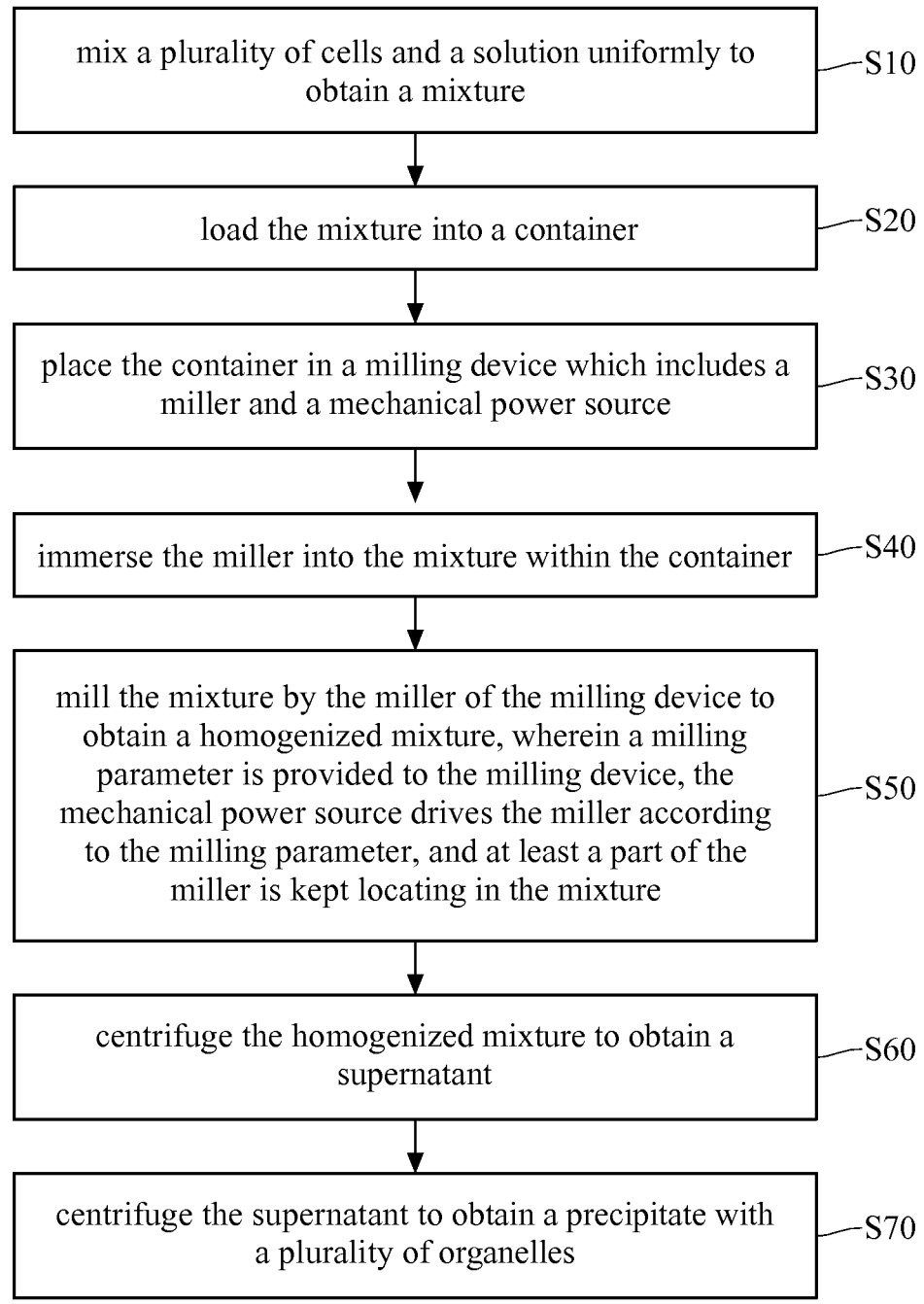
FIG. 1 is a flow chart of a method for extracting organelles from cells according to an embodiment of the disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawings.

A method for obtaining cells used in the disclosure to extract organelles is described herein. The cells adopted to extract organelles can be cells cultured in flasks. For example, cells are animal cells adhered to an inner surface of T75 flask, and the numbers of the cells in the T75 flask is more than $1 \times 10^8$. The cells can also be cultured in petri dishes.

First, a used culture medium in the flask is removed by a suction device. The suction device, for example, is an eppendorf. The culture medium, for example, is Dulbecoo's modification of Eagle's medium (DMEM) containing 10 wt % fetal bovine serum (FBS).

Next, an appropriate amount of phosphate buffered saline (PBS) is added into the flask by the suction device, and then the flask is gently shaken so that metabolic waste products that are adhered to cell membranes of the cells are removed by the PBS. Then, the PBS and the metabolic waste products both are removed from the flask by the suction device. The processes of adding the PBS into the flask, shaking the flask and removing the PBS and the metabolic waste products can be repeated several times to enhance the effort of removing the metabolic waste products. An amount of the PBS added into the T75 flak, for example, is between 1 milliliter (ml) and 5 ml. In one embodiment, the amount of PBS added into the T75 flak is 3 ml. In addition, when the cells are cultured in a T175 flask which has larger inner surface area for the cells to adhere than the T75 flask, and the amount of PBS added into the T175 flak can be 10 ml.

Next, an appropriate amount of trypsin is added into the flask by the suction device, and the flask is kept in a sterile environment at 37° C. for 3 minutes to 5 minutes. Therefore, peptide bonds connecting the cell membranes and the inner surface of the flask are cut by a hydrolysis reaction of the peptide bonds and the trypsin so that the cells are separated from the inner surface of the flask. For example, an amount of the trypsin added into the T75 flak is between 1 ml and 3 ml. In one embodiment, the amount of the trypsin added into the T75 flak is 1 ml. In addition, when the cells are cultured in the T175 flask, the amount of the trypsin added into the T175 flak can be 5 ml.

Next, an appropriate amount of an unused culture medium is added into the flask by the suction device for stopping the hydrolysis reaction of the trypsin, and then the cells and the culture medium in the flask are moved into a centrifuge tube by the suction device. For example, an amount of the unused culture medium added into the T75 flak is between 1 ml and 3 ml. In an embodiment, the amount of the unused culture medium added into the T75 flak is 2 ml. In addition, when the cells are cultured in the T175 flask, the amount of the unused culture medium added into the T175 flak can be 5 ml. In addition, the capacity of the centrifuge tube is 15 ml.

Next, the cells and the culture medium in the centrifuge tube are centrifuged by a centrifugal force of 300 G at 22° C. for 5 minutes so that the cells are deposited at a bottom part of the centrifuge tube. Then, a supernatant in the centrifuge tube is removed by the suction device after centrifuging the cells and the culture medium in the centrifuge tube.

Next, an appropriate amount of a SEH buffer solution is added into the centrifuge tube before the cells and the SEH buffer solution in the centrifuge tube is centrifuged by a centrifugal force of 300 G at 22° C. for 5 minutes for cleaning the cells. After centrifuging the cells and the SEH buffer solution in the centrifuge tube, a supernatant in the centrifuge tube is removed by the suction device, and the cells deposited at the bottom part of the centrifuge tube are used for extracting organelles in the following descriptions. The processes of adding the SEH buffer solution into the centrifuge tube, centrifuging the cells and the SEH buffer solution in the centrifuge tube and removing the supernatant in the centrifuge tube can be repeated several times to enhance the cleaning effort. For example, the amount of the SEH buffer solution added into the centrifuge tube is between 1 ml and 3 ml. In an embodiment, the amount of the SEH buffer solution added into the centrifuge tube is 3 ml.

The SEH buffer solution is used for maintaining the structure stability of an outer membrane and an inner membrane of the organelles immersed in the SEH buffer solution. The SEH buffer solution includes sucrose, ethylene glycol-bis(2-aminoethylether)-N,N,N',N'-tetra-acetic acid (EGTA) and 2-[4-(2-hydroxyethyl)piperazin-1-yl]ethane-sulfonic acid (HEPES). A molar concentration of the sucrose in the SEH buffer solution is 0.25 M. A molar concentration of the EGTA in the SEH buffer solution is 0.5 mM. A molar concentration of the HEPES in the SEH buffer solution is 3 mM. A pH value of the SEH buffer solution is 7.2, and the pH value is adjusted by NaOH solution and HCl solution. The SEH buffer solution has to be approximately stored at 4° C.

An operating temperature of the process of obtaining the cells described above are equal to or lower than 4° C. except particular processes with specific operating temperature limitations. As a result, containers, such as the flask and the centrifuge tube, and solutions, such as the culture medium, the PBS, the trypsin and the SEH buffer solution, have to be chilled to equal to or lower than 4° C. For example, the containers and the solutions are placed in crushed ice or ice bricks before and during operation so that the containers and the solutions are chilled to and maintained at 4° C. before and during the processes. Therefore, a denaturation of proteins in the cells and organelles due to rise in temperature during the processes can be avoided. However, the disclosure is not limited to the above-mentioned temperature. The operating temperature can be altered according to different types of the cells or types of the proteins.

Figure 2:
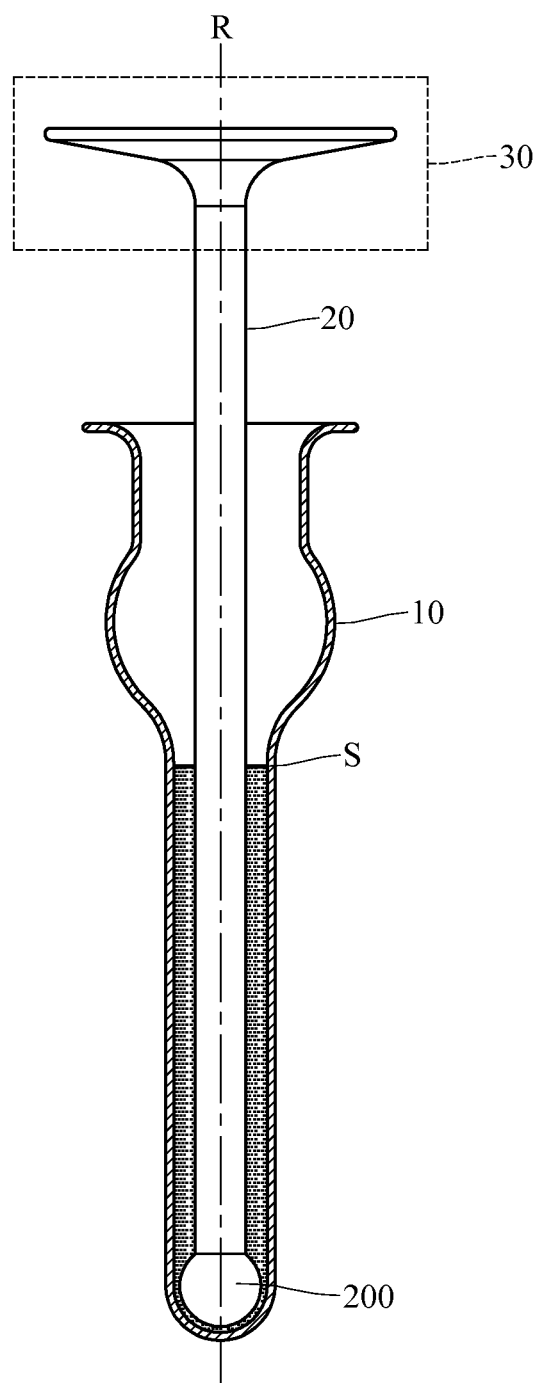
FIG. 2 is an exemplary schematic cross-sectional view of a miller which mills a mixture according to the embodiment of the disclosure.

The following describes the method of extracting organelles from cells of the present disclosure. Please refer to FIG. 1 and FIG. 2. FIG. 1 is a flow chart of a method for extracting organelles from cells according to an embodiment of the disclosure. FIG. 2 is an exemplary schematic cross-sectional view of a miller which mills a mixture according to the embodiment of the disclosure.

First, a plurality of cells and a solution are mixed uniformly to obtain a mixture (step S10). In detail, the cells deposited at the bottom part of the centrifuge tube and the solution are loaded into a mixing container. Then, the solution in the mixing container is suctioned and released repeatedly by the suction device to mix the plurality of cells deposited at the bottom part of the mixing container and the solution uniformly to obtain the mixture. The solution in step S10, for example, is the SEH buffer solution or the DMEM medium, and a volume of the solution loaded into the mixing container is 1 ml to 5 ml. The mixing container can be an unused clean centrifuge tube or the original centrifuge tube filled with the cells in the above-mentioned process.

After step S10 is finished, 10 to 40 microlitres (μl) of the mixture from the container can be placed in a device for cell counting to determine a cell number of the cells in the mixture. In one embodiment, 20 μl of the mixture from the container is taken out of the mixing container for determining the cell number of the cells in the mixture.

Next, the mixture is loaded into a container (step S20). In detail, a part of the mixture or all the mixture in step S10 is loaded into a milling container. A cell number of the cells in the milling container is equal to or more than $1 \times 10^7$ to obtain a better milling effect. In one embodiment, the cell number of the cells in the milling container is between $1 \times 10^7$ and $2 \times 10^7$ so as to obtain the better milling effect. The milling container 10 can be a milling tube shown in FIG. 2.

Next, the container is placed in a milling device which includes a miller and a mechanical power source (step S30). In detail, the miller and the mechanical power source are connected with each other. The miller 20 of the milling device can be the milling rod shown in FIG. 2. The mechanical power source 30 of the milling device shown in FIG. 2, for example, is a hydraulic motor or a cylinder.

Next, the miller is immersed into the mixture within the container (step S40). In detail, the miller is immersed into the mixture in the container slowly to avoid bringing air into the mixture to form bubbles in the mixture when the miller contacts the interface of the mixture and air. Therefore, damages of the organelles caused by an impact force generated by breaking down of the bubbles in the mixture are reduced so that a completeness of the organelles extracted from the cells is increased. In one embodiment of the disclosure, the mixture is loaded into the milling container, and then the miller is immersed into the mixture in the container foe milling. However, the disclosure is not limited to the order of loading the mixture into the container and putting the miller into the milling container. In other embodiment of the disclosure, the miller is put into the milling container before the mixture is slowly loaded into the container and covers a part of the miller.

Next, the mixture is milled by the miller of the milling device to obtain a homogenized mixture. A milling parameter is provided to the milling device, the mechanical power source drives the miller according to the milling parameter, and at least a part of the miller is kept in the mixture (step S50). In detail, the milling parameter provided to the milling device including a rotation parameter and a pressing parameter. As shown in FIG. 2, the mechanical power source 30 of the milling device drives the milling container 10 to rotate relative to the miller 20 along a rotation axis R according to the rotation parameter. The rotation axis R is the central axis of the milling container 10. The mechanical power source 30 of the milling device drives a milling head 200 of the miller 20 to reciprocate relative to the milling container 10 along the rotation axis R in the mixture according to the pressing parameter. A distance between an inner surface of the milling container 10 and the milling head 200 of the miller 20 is less than 0.1 millimeter (mm). Therefore, the cell membrane of the cells are ruptured by rubbing over an inner surface of the milling container 10 or a surface of the miller 20 when the miller 20 and the milling head 200 rotates and reciprocates relative to the milling container 10. As a result, the organelles in the cells go through the ruptured cell membranes of the cells and are uniformly distributed in the solution so that the homogenized mixture is obtained. In this disclosure, at least a part of the miller 20 is kept in the mixture during the process of milling the mixture. Specifically, as shown in FIG. 2, the milling head 200 is kept under a liquid level S of the mixture during the process of milling the mixture. Therefore, a situation that the milling head 200 brings air into the mixture to generate bubbles in the mixture when the milling head 200 contacts the interface of the mixture and air is avoided. As a result, damages of the organelles due to the impact force generated by breaking down of the bubbles in the mixture are reduced so that the completeness of the organelles extracted from the cells is increased.

Furthermore, the rotation parameter of the milling parameter described above is between 3 revolutions per minute (RPM) and 7 RPM. The pressing parameter of the milling parameter described above is between 19.6 newton (N) and 49 N. The miller reciprocates relative to the milling container along the central axis of the milling container in the milling container 10 times to 20 times. However, the disclosure is not limited to a rotation speed of the milling container relative to the miller, a pressing stress and a number of reciprocation of the miller. In other embodiment of the disclosure, the parameters described above can be altered to obtain the homogenized mixture with 80%~90% of cells ruptured when the process of milling the mixture is stopped. In one embodiment of the disclosure, the milling device, for example, is a Dounce homogenizer. In the embodiment of the disclosure, the mechanical power source drives the milling container to rotate relative to the miller. However, the disclosure is not limited to which component the mechanical power is applied. In other embodiment of the disclosure, the mechanical power source drives the miller to rotate and reciprocate relative to the milling container.

The mixture is observed by an optical microscope after a vital stain is added into the mixture in order to determine when to stop the process of milling the mixture. In detail, the vital stain, such as trypan blue, is added into a mixture removed from the mixture in the milling container, and then the mixture containing the vital stain is observed with the optical microscope. The vital stain added into the mixture enters the cells in the mixture. The vital stain is excluded by living cells but staying in dead cells whose cell membranes are ruptured. It can be understood that 80%~90% of the cells in the mixture being ruptured and stained means that there are enough numbers of organelles, which has left the cells by passing through the ruptured cell membranes and being uniformly distributed in the mixture, to perform the next process. Thus, when 80%~90% of the cells in the mixture are ruptured and stained, the process of milling the mixture can be stopped.

Next, the homogenized mixture is centrifuged to obtain a supernatant (step S60). In detail, the homogenized mixture is loaded into the centrifuge tube from the milling container before being centrifuged by a centrifugal force of 1000 G at 4° C. for 10 minutes. The homogenized mixture loaded in the centrifuge tube is centrifuged for 1 to 3 times. After the homogenized mixture is centrifuged, the living cells and the large and heavy fragments of the dead cells in the homogenized mixture are deposited at a bottom part of the centrifuge tube, and the organelles and the small and light fragments of the dead cells are suspending in the supernatant. Then, the supernatant including organelles, the small and light fragments of the dead cells and the solution is suctioned by the suction device and loaded into another centrifuge tube.

Last, the supernatant is centrifuged to obtain a precipitate with a plurality of organelles (step S70). In detail, the supernatant is centrifuged by a centrifugal force of 7000 G at 4° C. for 15 minutes. The supernatant loaded in the centrifuge tube is centrifuged for 1 to 3 times. After the supernatant is centrifuged, the organelles which are heavier than the small and light fragments of the dead cells are deposited at a bottom part of the centrifuge tube. The organelles become a part of the precipitate and are separated from a supernatant. Then, the supernatant is removed by the suction device and an appropriate amount of an unused solution such as SEH buffer solution is added into the centrifuge tube. After the unused solution is added into the centrifuge tube, the solution in the centrifuge tube is suctioned and released repeatedly by the suction device to mix the precipitate containing the organelles and the solution uniformly. The appropriate amount of the solution is determined by the cell number of the cells in step S10. For example, when the cell number of the cells in step S10 is between $1\times10^7$ and $2\times10^7$, 50 μl of the solution is added into the centrifuge tube.

After step S70, a 1:100 dilution of a conventional concentrated protease inhibitor is added into the centrifuge tube for storing the organelles. The organelles mixed with the solution, such as SEH buffer solution, and the protease inhibitor are stored at 4° C.

An operating temperature of the step S10 to the step S70 described above are equal to or lower than 4° C. As a result, containers, such as the mixing container, the milling container and the centrifuge tube, and solutions, such as the SEH buffer solution, have to be chilled to equal to or lower than 4° C. For example, the milling container and the miller are placed in crushed ice or ice bricks before and during the step S50 so that the milling container and the miller are chilled to and maintained at 4° C. before and during the processes. Therefore, a denaturation of the protein in the cells and organelles due to rise in temperature during the processes can be avoided. However, the disclosure is not limited to the operating temperature. The operating temperature can be altered according to different types of the proteins in the cells and the organelles.

In addition, a concentration of the complete organelles extracted from the cells in the SEH buffer solution can be determined by protein concentration determination using a bovine serum albumin (BSA) as a protein concentration standard. During the protein concentration determination, the BSA standard samples which have BSA concentrations of 0 microgram per microlitre (μg/μl), 0.25 μg/μl, 0.5 μg/μl, 1 μg/μl, 1.5 μg/μ and 2 μg/μl and the organelles extracted from the cells are uniformly mixed with quantitation reagents, respectively, and then kept at 37° C. for 30 minutes. Next, absorbance values of the BSA standard samples are measured and a calibration curve representing absorbance as a function of concentration is formed. Last, absorbance value of the organelles is measured and compared with the calibration curve to obtain the concentration of the organelles by interpolation.

The followings are two embodiments of the disclosure and two comparative examples described in detail, and the differences of the organelles extracted from the cells between the embodiments and the comparative examples are tested.

Example 1

First, $2 \times 10^7$ animal cells are added into 2 ml of SEH buffer solution to obtain a mixture. Organelles extracted from animal cells are mitochondria in example 1. Next, the mixture is loaded into a milling tube of a Dounce homogenizer. Next, a milling rod of the Dounce homogenizer is immersed into the mixture located in the milling tube.

Next, the mixture is milled in the milling tube by the milling rod to obtain a homogenized mixture. A milling head of the milling rod is kept in the mixture during the milling process. The rotation speed of the milling tube relative to the milling rod is 5 RPM. The pressing strength applied on the mixture by the milling head is 19.6 N. The milling head reciprocates in the mixture relative to the milling tube 15 times.

Next, the homogenized mixture is loaded into a centrifuge tube and the homogenized mixture is centrifuged in the centrifuge tube twice by a centrifugal force of 1000 G at 4° C. for 10 minutes. After the homogenized mixture is centrifuged in the centrifuge tube, a supernatant in the centrifuge tube is suctioned and moved into another centrifuge tube by a suction device.

Last, the supernatant in the centrifuge tube is centrifuged by a centrifugal force of 7000 G at 4° C. for 15 minutes to obtain a precipitate. After the supernatant is centrifuged in the centrifuge tube, a supernatant is removed in the centrifuge tube by the suction device and 50 ml of unused SEH buffer solution is added into the centrifuge tube. The SEH buffer solution in the centrifuge tube is suctioned and released by the suction device, repeatedly, so that the precipitate containing the organelles and the SEH buffer solution are mixed uniformly.

Example 2

The processes of extracting organelles from cells in example 2 are similar to the processes in example 1. The difference between example 1 and example 2 is the process of milling the mixture.

When the mixture is milled in the milling tube by the milling rod, the milling head of the milling rod is kept in the mixture during the milling process. The rotation speed of the milling tube relative to the milling rod is 5 RPM. The pressing strength applied on the mixture by the milling head is 49 N. The milling head reciprocates in the mixture relative to the milling tube 15 times.

Comparative Example 1

The processes of extracting organelles from cells in comparative example 1 are similar to the processes in example 1. The difference between example 1 and comparative example 1 is the process of milling the mixture.

When the mixture is milled in the milling tube by the milling rod, the milling head of the milling rod is not always kept in the mixture during the milling process. Specifically, when the milling head is moved away from the bottom of the milling tube, the milling head is pulled out from the mixture into air. When the milling head is moved toward the bottom of the milling tube, the milling head is inserted in to the mixture from air. The rotation speed of the milling tube relative to the milling rod is 5 RPM. The pressing strength applied on the mixture by the milling head is 19.6 N. The milling head reciprocates in the mixture relative to the milling tube for 15 times.

Comparative Example 2

The processes of extracting organelles from cells in comparative example 2 are similar to the processes in example 1. The difference between example 1 and comparative example 2 is the process of milling the mixture.

When the mixture is milled in the milling tube by the milling rod, the milling head of the milling rod is kept in the mixture during the milling process. The rotation speed of the milling tube relative to the milling rod is 5 RPM. The press applied on the mixture by the milling head is provided manually. The milling head reciprocates in the mixture relative to the milling tube for 15 times.

As shown in Table 1, the following are test results of the organelles obtained in example 1, example 2, comparative example 1 and comparative example 2. The concentration of mitochondrion in the mixture of the precipitate and the SEH buffer solution is determined by protein concentration determination using a bovine serum albumin (BSA) as a protein concentration standard. The completeness of the mitochondrion is observed by optical microscope.

TABLE 1

|  | Example 1 | Example 2 | Comparative example 1 | Comparative example 2 |
|---|---|---|---|---|
| Cell number | $2 \times 10^7$ | $2 \times 10^7$ | $2 \times 10^7$ | $2 \times 10^7$ |
| SEH buffer solution (ml) | 2.0 | 2.0 | 2.0 | 2.0 |
| Rotation speed of milling tube (rpm) | 5.0 | 5.0 | 5.0 | 5.0 |
| Pressing strength of milling head (N) | 19.6 | 49 | 19.6 | — |
| Driving source of milling rod | Mechanical | Mechanical | Mechanical | Manual |
| Reciprocate times of milling head | 15 | 15 | 15 | 15 |
| Milling head is kept in mixture | Yes | Yes | No | Yes |
| Operating temperature of milling | 4° C. | 4° C. | 4° C. | 4° C. |
| Concentration of mitochondrion | High | High | Low | Low |
| Completeness of mitochondrion | Good | Good | Rupture | Rupture |

The mitochondria obtained by the extracting method of the example 1 and the example 2 have higher mitochondrion concentration and better completeness than the mitochondria obtained by the extracting method of the comparative example 1 and the comparative example 2. In the example 1 and the example 2, at least part of the milling head is kept in the mixture so as to avoid generating bubbles in the mixture from the air which is bring into the mixture by the milling head. Therefore, damages of the organelles caused by the impact force generated by breaking down of the bubbles in the mixture are reduced. As a result, a milling efficiency and the completeness of the organelles are increased. In addition, the milling rod is drove by the mechanical power source so that the pressing can be provided stably. Therefore, using the mechanical power source to drive the milling rod can help to build a standard database of milling parameters to control the completeness of the mitochondrion extracted from the cells.

In comparison with the example 1 and the comparative example 1, the mitochondrion concentration is lower in the comparative example 1 than in the example 1, and the completeness of mitochondrion is worse in the comparative example 1 than in the example 1. The reason of the problems above is that the milling head of the milling rod is not always kept in the mixture during the milling process. A lot of bubbles may be generated from the air bringing into the mixture when the milling head leaves and enters the mixture during the milling process. Therefore, the impact force generated by breaking down of the bubbles in the mixture damages the organelles and lowers the milling efficiency.

In comparison with the example 1 and the comparative example 2, the mitochondrion concentration is lower in the comparative example 2 than in the example 1, and the completeness of mitochondrion is worse in the comparative example 2 than in the example 1. The reason of the problems above is that the milling rod is driven manually to reciprocate relative to the milling tube so that the milling stress and the moving direction of the milling rod are difficult to maintain consistently. Therefore, the concentration and the completeness of the mitochondrion are difficult to maintain the consistency.

According to the method of extracting organelles from cells disclosed in the embodiments of the disclosure, the mixture is milled to obtain a homogenized mixture by rotating a miller relative to the container along a central axis of the container as a rotating axis and reciprocating the miller relative to the container along the central axis of the container and at least a part of the miller being kept locating in the mixture. Accordingly this solves the problem that the membranes of the organelles are also damaged when the cell membranes are ruptured.

Moreover, with appropriate parameters which include pressing strength, rotation speed, and operating temperature, the method of extracting organelles from cells disclosed in the embodiments of the disclosure can keep the completeness of the organelles when a large number of the cell membranes are broken. Therefore, the method of extracting organelles from cells disclosed in the embodiments of the disclosure can extract a large number of the organelles having good completeness from the cells.

What is claimed is:

1. A method of extracting organelles from cells, comprising:
    mixing a plurality of cells and a solution uniformly to obtain a mixture;
    loading the mixture into a container;
    placing the container with the mixture inside in a milling device, wherein the milling device comprises a miller and a mechanical power source connected to the miller;
    immersing the miller into the mixture within the container;
    milling the mixture by the miller of the milling device to obtain a homogenized mixture, wherein a milling parameter is provided to the milling device, and the mechanical power source drives the miller according to the milling parameter;
    centrifuging the homogenized mixture to obtain a supernatant; and
    centrifuging the supernatant to obtain a precipitate with a plurality of organelles;
    wherein, when milling the mixture, at least a part of the miller is kept in the mixture.

2. The method of extracting organelles from cells of claim 1, wherein the step of milling the mixture by the miller of the milling device to obtain the homogenized mixture further comprises:
    controlling the mechanical power source by a rotation parameter of the milling parameter, and driving the container to rotate relative to the miller along a central axis of the container as a rotation axis by the mechanical power source; and
    controlling the mechanical power source by a pressing parameter of the milling parameter, and driving the miller to reciprocate along the central axis of the container in the container to mill the mixture by the mechanical power source.

3. The method of extracting organelles from cells of claim 2, wherein the rotation parameter is between 3 r evolutions per minute and 7 r evolutions per minute.

4. The method of extracting organelles from cells of claim 1, wherein the step of milling the mixture by the miller of the milling device to obtain the homogenized mixture further comprises:
    stopping the milling when 80% to 90% of the plurality of cells in the mixture is ruptured.

5. The method of extracting organelles from cells of claim 2, wherein the pressing parameter is between 19.6 newton (N) and 49 newton (N).

6. The method of extracting organelles from cells of claim 2, wherein the miller reciprocates along the central axis of the container in the container 10 times to 20 times.

7. The method of extracting organelles from cells of claim 1, wherein the solution is a buffer solution comprising sucrose, EGTA (ethylene glycol-bis(2-aminoethylether)-N, N,N',N'-tetra-acetic acid) and HEPES (2-[4-(2-hydroxyethyl)piperazin-1-yl]ethanesulfonic acid), a molar concentration of sucrose in the buffer solution is 0.25 M, a molar concentration of EGTA in the buffer solution is 0.5 mM and a molar concentration of HEPES in the buffer solution is 3 mM.

8. The method of extracting organelles from cells of claim 1, wherein an operating temperature of all the steps is less than or equal to 4° C.

9. The method of extracting organelles from cells of claim 1, wherein the plurality of organelles is mitochondrion.

10. A method of extracting organelles from cells, comprising:
    mixing a plurality of cells and a solution uniformly to obtain a mixture;
    loading the mixture into a container;
    milling the mixture in the container to obtain a homogenized mixture by rotating a miller relative to the container along a central axis of the container as a rotating axis and reciprocating the miller relative to the container along the central axis of the container;
centrifuging the homogenized mixture to obtain a supernatant; and
centrifuging the supernatant to obtain a precipitate with a plurality of organelles;
wherein, when milling the mixture, at least a part of the miller is kept in the mixture.

* * * * *